United States Patent
Kearns

(10) Patent No.: US 10,765,833 B2
(45) Date of Patent: Sep. 8, 2020

(54) URINARY CATHETER ASSEMBLIES WITH FUNNEL-MOUNTED GRIPPING MEMBER

(71) Applicant: Hollister Incorporated, Libertyville, IL (US)

(72) Inventor: Barbara J. Kearns, Balla (IE)

(73) Assignee: Hollister Incorporated, Libertyville, IL (US)

( * ) Notice: Subject to any disclaimer, the term of this patent is extended or adjusted under 35 U.S.C. 154(b) by 396 days.

(21) Appl. No.: 15/552,920

(22) PCT Filed: Jan. 21, 2016

(86) PCT No.: PCT/US2016/014273
§ 371 (c)(1),
(2) Date: Aug. 23, 2017

(87) PCT Pub. No.: WO2016/137613
PCT Pub. Date: Sep. 1, 2016

(65) Prior Publication Data
US 2018/0050173 A1    Feb. 22, 2018

Related U.S. Application Data

(60) Provisional application No. 62/121,542, filed on Feb. 27, 2015.

(51) Int. Cl.
*A61M 25/00* (2006.01)
*A61M 25/01* (2006.01)

(52) U.S. Cl.
CPC ...... *A61M 25/0017* (2013.01); *A61M 25/002* (2013.01); *A61M 25/0111* (2013.01)

(58) Field of Classification Search
CPC .......... A61M 25/0017; A61M 25/0111; A61M 25/002
See application file for complete search history.

(56) References Cited

U.S. PATENT DOCUMENTS 1,085,505 A * 1/1914 Stafford .................. E02D 3/068
                                                    404/133.1
1,977,180 A * 10/1934 Forbes ..................... A47L 13/24
                                                    403/100

(Continued)

FOREIGN PATENT DOCUMENTS

DE    20 2004 012420 U1    11/2004
EP    2 946 803 A1    11/2015

(Continued)

OTHER PUBLICATIONS

International Search Report and Written Opinion for PCT Patent Appl'n. No. PCT/US2016/014273, dated Apr. 1, 2016.

*Primary Examiner* — Adam Marcetich
(74) *Attorney, Agent, or Firm* — Cool Alex Ltd.

(57) ABSTRACT

A urinary catheter assembly includes a catheter shaft, a drainage funnel associated with the distal end of the catheter shaft, and a gripping member. The distal end of the gripping member is fixedly secured to the drainage funnel, while an extendable portion of the gripping member allows its proximal end to be moved along the length of the catheter shaft toward and away from the proximal end of the catheter shaft. The extendable portion of the gripping member encircles at least a portion of the catheter shaft when the proximal end of the gripping member is moved toward the proximal end of the catheter shaft, thereby allowing for the gripping member to be used to manipulate the catheter shaft without directly touching the catheter shaft.

19 Claims, 2 Drawing Sheets

(56) References Cited

U.S. PATENT DOCUMENTS

| | | | |
|---|---|---|---|
| 3,421,509 A | 1/1969 | Fiore | |
| 4,051,849 A | 10/1977 | Poncy et al. | |
| 4,371,043 A * | 2/1983 | Kubokawa | B24B 23/02 |
| | | | 173/162.2 |
| 4,700,978 A * | 10/1987 | Saum | F24B 1/1915 |
| | | | 294/176 |
| 4,725,267 A * | 2/1988 | Vaillancourt | A61M 5/3202 |
| | | | 604/192 |
| 4,830,059 A * | 5/1989 | Silberstang | F16L 11/10 |
| | | | 138/130 |
| 5,405,338 A * | 4/1995 | Kranys | A61M 25/005 |
| | | | 604/103.09 |
| 5,429,139 A * | 7/1995 | Sauter | A61M 25/09 |
| | | | 600/434 |
| 5,662,622 A * | 9/1997 | Gore | A61M 25/0012 |
| | | | 138/123 |
| 5,871,475 A | 2/1999 | Frassica | |
| 6,402,726 B1 | 6/2002 | Genese | |
| 6,464,632 B1 * | 10/2002 | Taylor | A61B 1/005 |
| | | | 138/174 |
| 8,523,823 B2 | 9/2013 | Ostfeld et al. | |
| 2003/0130564 A1 * | 7/2003 | Martone | A61B 1/00071 |
| | | | 600/121 |
| 2004/0152941 A1 * | 8/2004 | Asmus | A61M 25/09 |
| | | | 600/1 |
| 2004/0199112 A1 * | 10/2004 | Dalton | A61M 5/158 |
| | | | 604/110 |
| 2005/0033311 A1 * | 2/2005 | Guldfeldt | A61M 25/04 |
| | | | 606/108 |
| 2005/0131423 A1 * | 6/2005 | Yachia | A61F 2/88 |
| | | | 606/108 |
| 2006/0163097 A1 * | 7/2006 | Murray | A61M 25/0009 |
| | | | 206/364 |
| 2006/0247602 A1 | 11/2006 | Dulak et al. | |
| 2009/0299334 A1 * | 12/2009 | Nishtala | A61M 25/0017 |
| | | | 604/528 |
| 2010/0064860 A1 * | 3/2010 | Kozak | B25B 23/0028 |
| | | | 81/177.6 |
| 2010/0249748 A1 * | 9/2010 | Szucs | A61M 5/326 |
| | | | 604/506 |
| 2011/0114520 A1 * | 5/2011 | Matthison-Hansen | |
| | | | A61M 25/002 |
| | | | 206/364 |
| 2011/0224628 A1 * | 9/2011 | Bodenlenz | A61M 25/0012 |
| | | | 604/264 |
| 2012/0179144 A1 * | 7/2012 | Carleo | A61M 25/0017 |
| | | | 604/544 |
| 2012/0260463 A1 * | 10/2012 | Hines | B25G 1/102 |
| | | | 16/430 |
| 2013/0161227 A1 * | 6/2013 | Gustavsson | A61M 25/002 |
| | | | 206/571 |
| 2014/0045142 A1 * | 2/2014 | Becker | A61C 5/42 |
| | | | 433/102 |
| 2014/0046302 A1 * | 2/2014 | Green | A61M 25/09 |
| | | | 604/528 |
| 2014/0150782 A1 * | 6/2014 | Vazales | A61M 16/0463 |
| | | | 128/202.16 |
| 2014/0276661 A1 | 9/2014 | Hannon et al. | |
| 2015/0136942 A1 * | 5/2015 | Zayat | A45F 5/02 |
| | | | 248/690 |
| 2015/0343171 A1 * | 12/2015 | Hannon | A61M 25/0111 |
| | | | 604/544 |
| 2016/0184550 A1 * | 6/2016 | Adler | A61M 25/0023 |
| | | | 604/544 |

FOREIGN PATENT DOCUMENTS

| | | |
|---|---|---|
| WO | WO 99/25402 A1 | 5/1999 |
| WO | WO 2007/050685 A2 | 5/2007 |
| WO | WO 2010/006620 A1 | 1/2010 |
| WO | WO 2012/176189 A1 | 12/2012 |

* cited by examiner

URINARY CATHETER ASSEMBLIES WITH FUNNEL-MOUNTED GRIPPING MEMBER

RELATED APPLICATIONS

This application is a U.S. national stage application of PCT Patent Application Serial No. PCT/US2016/014273, filed Jan. 21, 2016, which claims the benefit of and priority of U.S. Provisional Patent Application Ser. No. 62/121,542, filed Feb. 27, 2015, the contents of which are incorporated by reference herein.

DESCRIPTION

Technical Field

The present disclosure generally relates to urinary catheter assemblies. More particularly, the present disclosure relates to urinary catheter assemblies having a funnel-mounted member for gripping a catheter shaft.

BACKGROUND

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day. Such catheters typically include a shaft that is sufficiently flexible to navigate the curves of the urethra (especially catheters intended for male users), yet rigid enough to be pushed through the urethra without collapsing or "snaking" before an end of the catheter reaches the bladder.

A primary concern when considering urinary catheters is the need to avoid contamination of the catheter shaft prior to and during advancement of the shaft into the urethra. In particular, if the catheter shaft is directly gripped by a user, then germs and bacteria from the hand of the user may be transferred to the shaft and then to the urethra. Accordingly, existing urinary catheters have been known to include one of a number of possible anti-contamination features. For example, it is known to provide a sleeve that extends between a proximal introducer tip and a distal funnel of the urinary catheter. The thin, film-like sleeve may be pressed against the catheter shaft by the user to grip and handle the shaft without directly contacting the shaft. According to another approach, a generally cylindrical or tubular gripper may surround a portion of the catheter shaft and be moved along the length of the shaft. The gripper may be squeezed or pinched to press its inner surface against the catheter shaft, thereby allowing a user to grip and handle the shaft without directly contacting it. Other approaches to hygienic handling of a urinary catheter are also known.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter assembly includes a catheter shaft extending between proximal and distal ends, with a drainage funnel associated with the distal end of the catheter shaft. The distal end of a gripping member is fixedly secured to the drainage funnel, with an extendable portion of the gripping member being configured to allow the proximal end of the gripping member to be moved along the length of the catheter shaft toward and away from the proximal end of the catheter shaft. The extendable portion of the gripping member encircles at least a portion of the catheter shaft when the proximal end of the gripping member is moved toward the proximal end of the catheter shaft.

In another aspect, a method is provided for using a urinary catheter assembly. According to the method, a drainage funnel associated with the distal end of a catheter shaft of the urinary catheter assembly is gripped. A gripping member including a distal end fixedly secured to the drainage funnel is also gripped. An extendable portion of the gripping member is extended along at least a portion of the catheter shaft toward the proximal end of the catheter shaft, and the proximal end of the catheter shaft is advanced into a urethra while gripping the gripping member.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
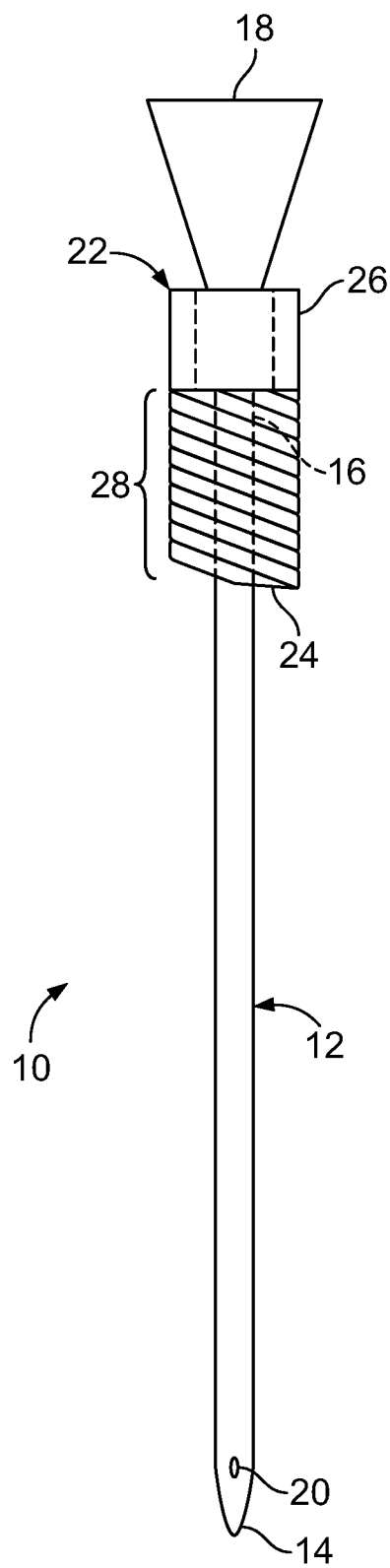
FIG. 1 is a front elevational view of a urinary catheter assembly according to an aspect of the present disclosure, having a gripping member in a least extended condition.
Figure 2:
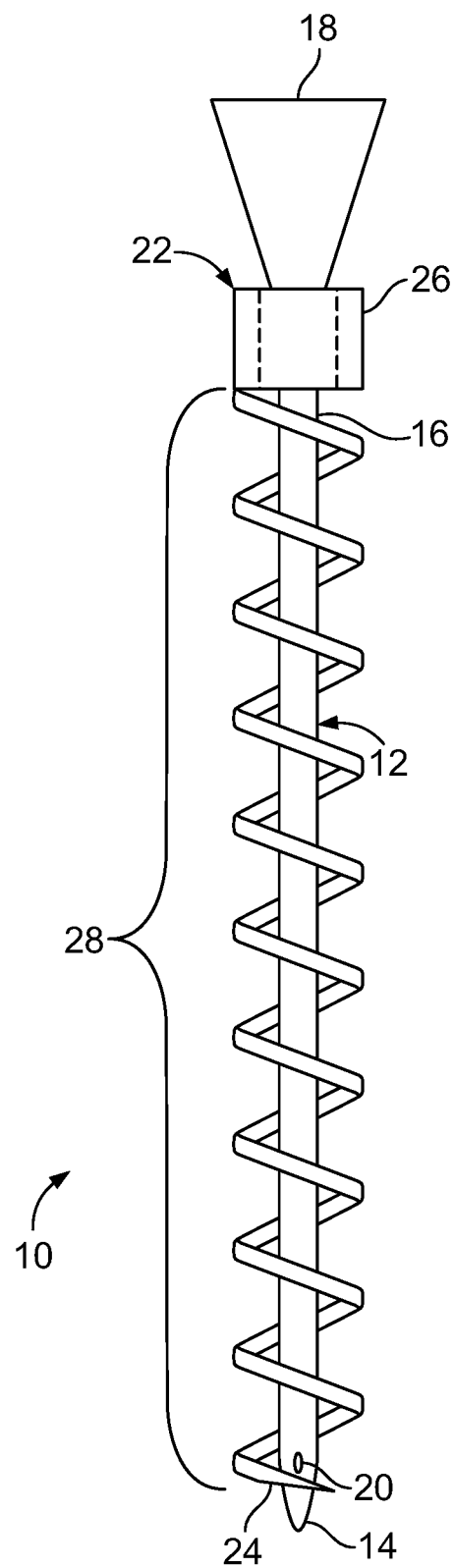
FIG. 2 is a front elevational view of the urinary catheter assembly of FIG. 1, with the gripping member in an extended condition.

FIGS. 1 and 2 show a urinary catheter assembly 10 according to the present disclosure. The urinary catheter assembly 10 is illustrated as a male catheter assembly, but it is within the scope of the present disclosure for the urinary catheter assembly 10 to be provided as a female catheter assembly.

The urinary catheter assembly 10 includes a catheter shaft 12, which may be provided as an elongated, hollow tube extending between a closed proximal end 14 and an open distal end 16, with a drainage funnel 18 associated with the distal end 16 of the catheter shaft 12. The catheter shaft 12 may include one or more eyes or openings 20 at or adjacent to the proximal end 14 of the catheter shaft 12 to drain urine from a bladder into the hollow interior of the catheter shaft 12, where it flows to the drainage funnel 18 to exit the urinary catheter assembly 10. The catheter shaft 12 and drainage funnel 18 may be provided according to conventional design, but it is also within the scope of the present disclosure for the catheter shaft 12 and/or the drainage funnel 18 to have a novel design.

The urinary catheter assembly 10 further includes a gripping member 22 associated with the drainage funnel 18 for improved handling of the catheter shaft 12, as will be described in greater detail. The gripping member 22 extends between a proximal end 24 and a distal end 26, with the distal end 26 of the gripping member 22 being fixedly secured to the drainage funnel 18 or to the distal end 16 of the catheter shaft 12. The mechanism for securing the gripping member 22 to the drainage funnel 18 may vary without departing from the scope of the present disclosure and may depend upon the material composition of the gripping member 22 and the drainage funnel 18. For example, the distal end 26 of the gripping member 22 may be fixedly secured to the drainage funnel 18 by an adhesive or by a weld or by a mechanical fastener or by an interference fit or the like. In another embodiment the gripping member 22 may be effectively affixed to the drainage funnel 18 by integrating the gripping member 22 into the drainage funnel 18 (i.e., by providing the drainage funnel 18 and gripping member 22 as a single piece, rather than as two separate pieces that are secured together).

Only part of the gripping member 22 is fixedly secured to the drainage funnel 18, while another part of the gripping member 22 (which is referred to herein as the extendable portion 28 and includes the proximal end 24 of the gripping member 22) being free to move relative to the drainage funnel 18. For example, FIG. 1 shows the gripping member 22 and extendable portion 28 in an un-extended or least extended condition, while FIG. 2 shows the gripping member 22 and extendable portion 28 in an extended condition. As can be seen in FIG. 2, the distal end 26 of the gripping member 22 remains secured to the drainage funnel 18 while the proximal end 24 of the gripping member 22 is moved along the length of the catheter shaft 12 to the proximal end 14 of the catheter shaft 12. In other embodiments, the degree of extension may vary, such as by providing a gripping member and extendable portion that may move the proximal end of the gripping member along the entire length of the catheter shaft and beyond the proximal end of the catheter shaft or by providing a gripping member and extendable portion that may move the proximal end of the gripping member along only a portion of the length of the catheter shaft.

The extendable portion 28 may be variously configured without departing from the scope of the present disclosure. Preferably, the extendable portion 28 is generally tubular to allow it to encircle at least a portion of the catheter shaft 12 when the proximal end 24 of the gripping member 22 has been moved toward the proximal end 14 of the catheter shaft 12. In the illustrated embodiment, the extendable portion 28 of the gripping member 22 encircles a distal portion of the catheter shaft 12 when the gripping member 22 and extendable portion 28 are in a least extended condition (FIG. 1), but it is also within the scope of the present disclosure for the extendable portion 28 to be positioned entirely distally of the catheter shaft 12 when in its least extended condition. It may also be advantageous for the extendable portion 28 to be not only extendable, but also sufficiently flexible to bend with and follow the movements of the catheter shaft 12, rather than restricting the ability of the catheter shaft 12 to be bent or deformed from its straight configuration of FIGS. 1 and 2. Additionally, it may be preferred for the gripping member 22 (or at least the extendable portion 28 thereof) to be formed of a resilient material that, after being moved to a more extended condition (e.g., being moved from the condition of FIG. 1 to FIG. 2) resiliently returns to a less extended condition when released (e.g., by automatically returning to the condition of FIG. 1 after being moved to the condition of FIG. 2 and then released).

Any of a number of materials may be used to manufacture a gripping member 22 (or at least the extendable portion 28 thereof) having the aforementioned characteristics, although it may be advantageous to use a material that, in addition to being flexible, is also soft. As will be described in greater detail herein, the extendable portion 28 is used to grip and manipulate the catheter shaft 12, which is why a soft material may be advantageous to avoid possibly damaging the catheter shaft 12 during use of the urinary catheter assembly 10. By way of example, in one embodiment, the gripping member 22 (or at least the extendable portion 28 thereof) is formed of a thermoplastic elastomer material. Other materials or combinations of materials may also be used without departing from the scope of the present disclosure.

Figure 3:
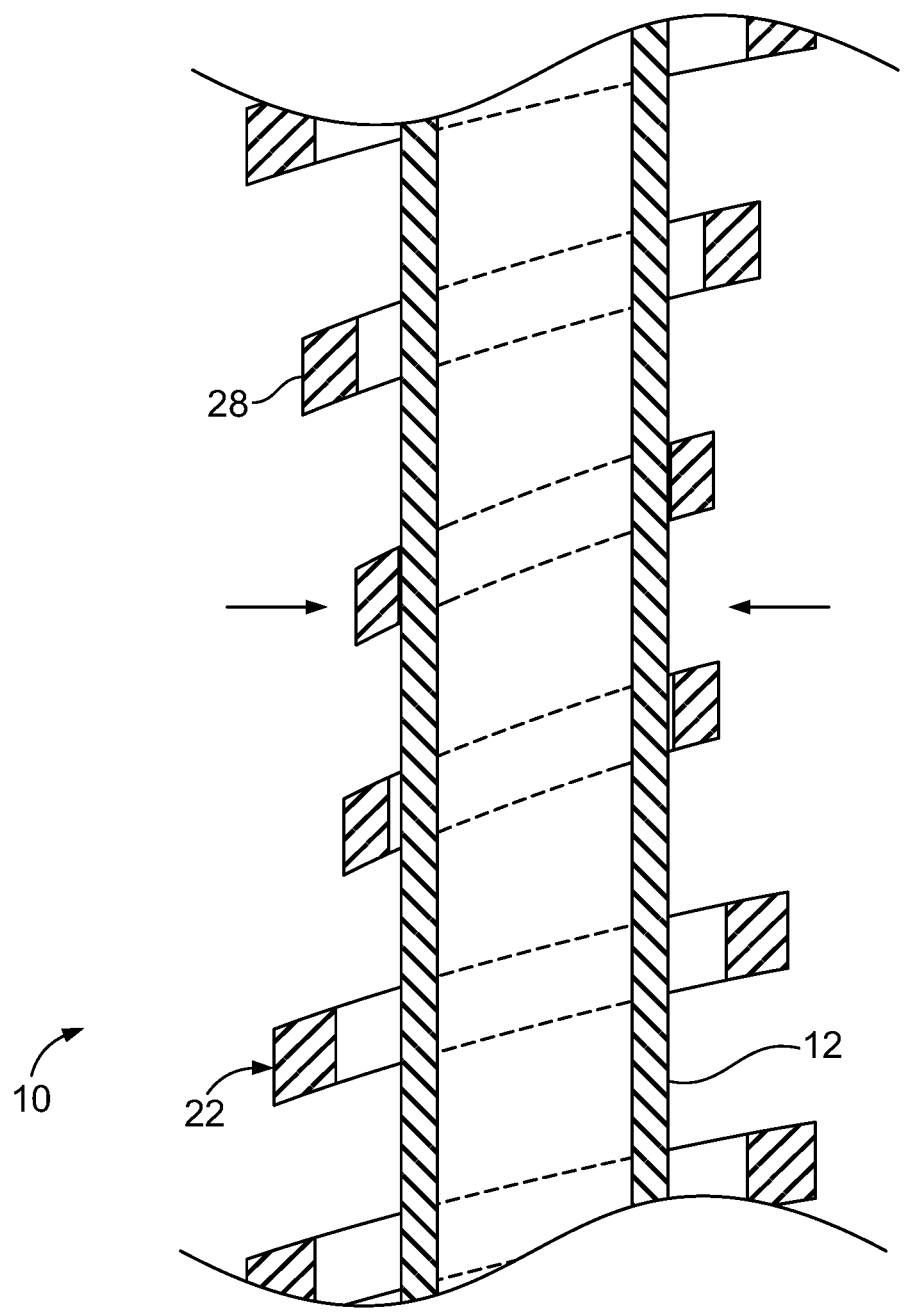
FIG. 3 is a cross-sectional, detail view of the urinary catheter assembly of FIG. 1, with the gripping member in an extended condition and pressed into contact with a catheter shaft of the urinary catheter assembly.

In the illustrated embodiment, the extendable portion 28 is configured as a helix or a coil, which may be stretched or extended (from the condition of FIG. 1 to the condition of FIG. 2, for example) to increase the space between adjacent turns of the helix. The number of turns of the helix, its extended and un-extended lengths, and its outer and inner diameters may vary without departing from the scope of the present disclosure, although it may be advantageous in general for the extendable portion 28 to have an inner diameter that is greater than the outer diameter of the catheter shaft 12 to create an at least small gap or separation therebetween. The illustrated extendable portion 28 is configured as a helical ribbon, with a generally rectangular cross-sectional shape, as best seen in FIG. 3). If so provided, it may be preferable for the cross-sectional shape of the helical ribbon to have a greater dimension in an axial direction (i.e., parallel to the length of the catheter shaft 12, or in the vertical direction in the orientation of FIG. 3) than in a radial direction (i.e., in the horizontal direction in the orientation of FIG. 3). By such a configuration, the relatively thin-walled extendable portion 28 is flexible, while provided more surface area in the axial direction for pinching the extendable portion 28 against the catheter shaft 12 without directly touching the catheter shaft 12 (as will be described in greater detail). It should be understood that the illustrated helical extendable portion 28 is merely one exemplary embodiment and that other configurations that allow for extension along the length of the catheter shaft 12 (e.g., a lattice pattern arranged in a tube around the catheter shaft 12 may also be employed without departing from the scope of the present disclosure.

The presence of the extendable portion 28 permits a user to manipulate the catheter shaft 12 without directly contacting (and potentially contaminating) it. In particular, a user may use the urinary catheter assembly 10 by first gripping the drainage funnel 18. The user may then grip the extendable portion 28 of the gripping member 22 and move it from an original condition (e.g., the least extended condition of FIG. 1) to a more extended condition, such as shown in FIG. 2. In the more extended condition, the user may then pinch or squeeze the extendable portion 28 to bring its inner surface into contact with the outer surface of the catheter shaft 12, as shown in FIG. 3. At this time, the user may release the drainage funnel 18 or continue gripping it.

By pinching or squeezing the extendable portion 28 against the catheter shaft 12, the user may effectively handle the catheter shaft 12 and direct its proximal end 14 into the urethra without directly touching the catheter shaft 12. For improved handling, it may be preferred to pinch or squeeze the extendable portion 28 against the catheter shaft 12 adjacent to the proximal end 14 of the catheter shaft 12, but it is within the scope of the present disclosure for the catheter shaft 12 to be gripped with the extendable portion 28 at any location along the length of the catheter shaft 12.

The user advances the proximal end 14 of the catheter shaft 12 into the urethra without any portion of the gripping member 22 entering into the urethra. When at least the proximal end 14 of the catheter shaft 12 has been advanced into the urethra, the user may release the gripping member 22 and then grip the drainage funnel 18 to further advance the catheter shaft 12 into the urethra. If the extendable portion 28 is resilient or otherwise biased to a less extended or least extended condition, then releasing the extendable portion 28 will cause it to automatically retract or pull the proximal end 24 of the gripping member 22 distally away from the proximal end 14 of the catheter shaft 12. If the extendable portion 28 is not resilient or biased to a less extended condition, then the user may manually move the proximal end 24 of the gripping member 22 distally away from the proximal end 14 of the catheter shaft 12 or allow the proximal end 24 of the gripping member 22 to press against the body, which has the effect of retracting the gripping member 22 as the catheter shaft 12 is advanced into the urethra.

In an alternative embodiment, rather than using the drainage funnel 18 alone to further advance the catheter shaft 12 through the urethra after its proximal end 14 has been introduced into the urethra, the gripping member 22 may aid in further advancing the catheter shaft 12 through the urethra. In particular, after the proximal end 14 of the catheter shaft 12 has been introduced into the urethra, the user may move the extendable portion 28 to a less extended condition, advance the catheter shaft 12 further into the urethra, and then repeat the process of moving the extendable portion 28 distally and proximally advancing the catheter shaft 12 until the catheter shaft 12 has been properly positioned within the urethra.

After the urinary catheter assembly 10 has been used to drain urine from the bladder, the user may grip the drainage funnel 18 and move it distally away from the body to withdraw the catheter shaft 12 from the urethra. Alternatively, the extendable portion 28 of the gripping member 22 may be pinched against a portion of the catheter shaft 12 positioned outside of the urethra and moved distally to withdraw the catheter shaft 12 from the urethra. Finally, the urinary catheter assembly 10 may be disposed of (e.g., placed into a toilet if it is formed of a water-degradable material or otherwise placed into a garbage receptacle) or sterilized and reused.

Aspects of the present subject matter described above may be beneficial alone or in combination with one or more other aspects. Without limiting the foregoing description, in accordance with one aspect of the subject matter herein, there is provided a urinary catheter assembly, which includes a catheter shaft, a drainage funnel, and a gripping member. The catheter shaft extends between proximal and distal ends, with the drainage funnel being associated with the distal end of the catheter shaft. The distal end of the gripping member is fixedly secured to the drainage funnel, while an extendable portion of the gripping member is configured to allow the proximal end of the gripping member to be moved along the length of the catheter shaft toward and away from the proximal end of the catheter shaft. The extendable portion of the gripping member encircles at least a portion of the catheter shaft when the proximal end of the gripping member is moved toward the proximal end of the catheter shaft.

In accordance with another aspect which may be used or combined with the preceding aspect, the gripping member is formed of a thermoplastic elastomer material.

In accordance with another aspect which may be used or combined with any of the preceding aspects, the extendable portion of the gripping member is configured to allow the proximal end of the gripping member to be moved to the proximal end of the catheter shaft.

In accordance with another aspect which may be used or combined with any of the preceding aspects, the extendable portion of the gripping member is configured as a helix.

In accordance with another aspect which may be used or combined with any of the preceding aspects, the extendable portion of the gripping member comprises a helical ribbon.

In accordance with another aspect which may be used or combined with any of the preceding aspects, the extendable portion of the gripping member is configured to be moved toward and into contact with the catheter shaft.

In accordance with another aspect which may be used or combined with any of the preceding aspects, the extendable portion of the gripping member is configured to resiliently move from an extended condition to a less extended condition.

In accordance with another aspect which may be used or combined with any of the preceding aspects, at least a portion of the extendable portion of the gripping member encircles the catheter shaft when the extendable portion is in a least extended condition.

In accordance with another aspect, there is provided a method for using a urinary catheter assembly. The method includes gripping a drainage funnel associated with the distal end of a catheter shaft of a urinary catheter assembly. A gripping member including a distal end fixedly secured to the drainage funnel is also gripped. An extendable portion of the gripping member is extended along at least a portion of the catheter shaft toward a proximal end of the catheter shaft, and the proximal end of the catheter shaft is advanced into a urethra while gripping the gripping member.

In accordance with another aspect which may be used or combined with the preceding aspect, the gripping member is formed of a thermoplastic elastomer material.

In accordance with another aspect which may be used or combined with any of the preceding two aspects, extending the extendable portion of the gripping member includes moving the proximal end of the gripping member to the proximal end of the catheter shaft.

In accordance with another aspect which may be used or combined with any of the preceding three aspects, gripping the gripping member includes gripping a gripping member having an extendable portion configured as a helix.

In accordance with another aspect which may be used or combined with any of the preceding four aspects, gripping the gripping member includes gripping a gripping member having an extendable portion comprising a helical ribbon.

In accordance with another aspect which may be used or combined with any of the preceding five aspects, the extendable portion of the gripping member is moved toward and into contact with the catheter shaft before advancing the proximal end of the catheter shaft into a urethra.

In accordance with another aspect which may be used or combined with any of the preceding six aspects, the gripping member is released after advancing the proximal end of the catheter shaft into a urethra, thereby resiliently moving the gripping member from an extended condition to a less extended condition.

In accordance with another aspect which may be used or combined with any of the preceding seven aspects, extending an extendable portion of the gripping member includes moving the extendable portion from a least extended condition in which at least a portion of the extendable portion encircles the catheter shaft.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A urinary catheter assembly, comprising:
    a catheter shaft extending between proximal and distal ends;
    a drainage funnel associated with the distal end of the catheter shaft; and
    a gripping member extending between proximal and distal ends, wherein
        the distal end of the gripping member is fixedly secured to the drainage funnel,
        an extendable portion of the gripping member is configured to allow the proximal end of the gripping member to be moved along the length of the catheter shaft toward and away from the proximal end of the catheter shaft,
        the extendable portion of the gripping member encircles at least a portion of the catheter shaft when the proximal end of the gripping member is moved toward the proximal end of the catheter shaft, and
        the extendable portion of the gripping member is resilient and consists only of a helix or a lattice structure arranged in a tube around the catheter shaft.

2. The urinary catheter assembly of claim 1, wherein the gripping member is formed of a thermoplastic elastomer material.

3. The urinary catheter assembly of claim 1, wherein the extendable portion of the gripping member is configured to allow the proximal end of the gripping member to be moved to the proximal end of the catheter shaft.

4. The urinary catheter assembly of claim 1, wherein the extendable portion of the gripping member is configured as a helical ribbon.

5. The urinary catheter assembly of claim 1, wherein the extendable portion of the gripping member is configured to be moved toward and into contact with the catheter shaft.

6. The urinary catheter assembly of claim 1, wherein at least a portion of the extendable portion of the gripping member encircles the catheter shaft when the extendable portion is in a least extended condition.

7. The urinary catheter assembly of claim 1, wherein the catheter shaft is configured for use in a male urethra.

8. The urinary catheter assembly of claim 1, wherein the catheter shaft is configured for use in a female urethra.

9. The urinary catheter assembly of claim 1, wherein the distal end of the gripping member is fixedly secured to the drainage funnel by an adhesive.

10. The urinary catheter assembly of claim 1, wherein the distal end of the gripping member is fixedly secured to the drainage funnel by a weld.

11. The urinary catheter assembly of claim 1, wherein the distal end of the gripping member is fixedly secured to the drainage funnel by a mechanical fastener.

12. The urinary catheter assembly of claim 1, wherein the distal end of the gripping member is fixedly secured to the drainage funnel by an interference fit.

13. The urinary catheter assembly of claim 1, wherein the gripping member is integrated into the drainage funnel as a single piece.

14. A method of using a urinary catheter assembly comprising:
    gripping a drainage funnel associated with a distal end of a catheter shaft of a urinary catheter assembly;
    gripping a gripping member including a distal end fixedly secured to the drainage funnel;
    extending an extendable portion of the gripping member along at least a portion of the catheter shaft toward a proximal end of the catheter shaft; and
    advancing the proximal end of the catheter shaft into a urethra while gripping the gripping member, wherein the extendable portion of the gripping member is
        configured as a helix or provided in a lattice pattern arranged in a tube around the catheter shaft and
        configured to resiliently move from an extended condition to a substantially collapsed condition.

15. The method of claim 14, wherein said gripping member is formed of a thermoplastic elastomer material.

16. The method of claim 14, wherein said extending an extendable portion of the gripping member includes moving a proximal end of the gripping member to the proximal end of the catheter shaft.

17. The method of claim 14, wherein said extendable portion of the gripping member comprises a helical ribbon.

18. The method of claim 14, further comprising moving the extendable portion of the gripping member toward and into contact with the catheter shaft prior to said advancing the proximal end of the catheter shaft into a urethra.

19. The method of claim 14, wherein said extending an extendable portion of the gripping member includes moving the extendable portion from a least extended condition in which at least a portion of the extendable portion encircles the catheter shaft.

* * * * *